(12) United States Patent
Jung et al.

(10) Patent No.: US 6,426,171 B1
(45) Date of Patent: Jul. 30, 2002

(54) PHOTORESIST MONOMER, POLYMER THEREOF AND PHOTORESIST COMPOSITION CONTAINING IT

(75) Inventors: Min Ho Jung; Jae Chang Jung; Geun Su Lee; Ki Ho Baik, all of Kyoungki-do (KR)

(73) Assignee: Hyundai Electronics Industries Co., Ltd. (KR)

( * ) Notice: Subject to any disclaimer, the term of this patent is extended or adjusted under 35 U.S.C. 154(b) by 0 days.

(21) Appl. No.: 09/627,714

(22) Filed: Jul. 28, 2000

(30) Foreign Application Priority Data

Jul. 30, 1999 (KR) .............................. 99-31303
Jul. 30, 1999 (KR) .............................. 99-31304

(51) Int. Cl.[7] .................... G03F 7/004; C08F 10/00; C07C 69/74
(52) U.S. Cl. ................. 430/270.1; 430/326; 526/281; 560/120
(58) Field of Search .................. 430/270.1, 326; 526/281, 282; 560/120

(56) References Cited

PUBLICATIONS

CA65:12122d CAOLD, Koch, H. et al.*
Monatsh, Chem., Koch, H. et al. 1965 96(6), 2000–4.*

* cited by examiner

*Primary Examiner*—Rosemary Ashton
(74) *Attorney, Agent, or Firm*—Townsend and Townsend and Crew LLP

(57) ABSTRACT

The present invention provides novel bicyclic photoresist monomers, and photoresist copolymer derived from the same. The bicyclic photoresist monomers of the present invention are represented by the formula:

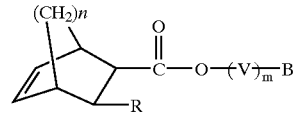

where m, n, R, V and B are those defined herein. The photoresist composition comprising the photoresist copolymer of the present invention has excellent etching resistance and heat resistance, and remarkably enhanced PED stability (post exposure delay stability).

26 Claims, No Drawings

PHOTORESIST MONOMER, POLYMER THEREOF AND PHOTORESIST COMPOSITION CONTAINING IT

BACKGROUND OF THE INVENTION

1. Field of the Invention

The present invention relates to novel photoresist monomers, polymers formed therefrom, and photoresist compositions containing the same. In particular, the present invention is directed to a bicyclic photoresist monomer compound comprising an amine group. Moreover, the present invention is also directed to polymers, and a photoresist compositions derived from the bicyclic photoresist monomers, and uses thereof, such as in photolithography processes using a DUV (deep ultraviolet) light source for preparing highly integrated semiconductor devices.

2. Description of the Background Art

Recently, chemical amplification type DUV photoresists have been investigated for achieving a high sensitivity in minute image formation processes for preparing semiconductor devices. Such photoresists are typically prepared by blending a photoacid generator and a matrix resin polymer having an acid labile group. The resolution of a lithography process depends, among others, on the wavelength of the light source, i.e., shorter the wavelength, smaller the pattern formation.

In general, a useful photoresist (hereinafter, abbreviated as "PR") has a variety of desired characteristics, such as an excellent etching resistance, heat resistance and adhesiveness. Moreover, the photoresist should be easily developable in a readily available developing solution, such as 2.38% aqueous tetramethylammonium hydroxide (TMAH) solution. However, it is very difficult to synthesize a photoresist polymer, especially DUV photoresist, which meets all of these desired characteristics. For example, a polymer having a polyacrylate polymer backbone are readily available, but it has a poor etching resistance and is difficult to develop. In order to increase its etching resistance, several groups have added an alicyclic unit to the polymer backbone. However, photoresist copolymers comprising entirely of an alicyclic polymer backbone is difficult to form.

To solve some of the problems described above, Bell Research Center developed a polymer having the following chemical formula:

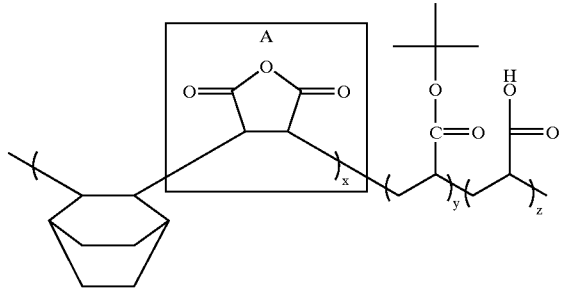

where the polymer backbone is substituted with a norbornene, an acrylate and a maleic anhydride unit. Unfortunately, even in the unexposed regions, the maleic anhydride moiety ('A' portion) dissolves readily in 2.38 wt % aqueous TMAH solution. Therefore, in order to inhibit the dissolution of the polymer in the unexposed section, the ratio of 'Y' portion having the tert-butyl substituent must be increased, but this increase results in a relative decrease in the 'Z' portion, which is responsible for the adhesiveness of the photoresist polymer. This decrease in the relative amount of the 'Z' portion may result in separation of the photoresist from the substrate during a pattern formation.

In order to circumvent the dissolution problem of maleic anhydride, cholesterol type dissolution inhibitors have been added to photoresist polymers to form a two-component system. Unfortunately, the addition of this dissolution inhibitor [about 30%(w/w) of the resin] resulted in, among others, poor reappearance, high production cost, poor adhesiveness, and a severe top-loss of the resist in the etching process resulting in a poor pattern formation.

Despite these difficulties, a variety of photoresist polymers with improved etching resistance, adhesiveness and resolution have been developed. Unfortunately, however, most chemically-amplified photoresists currently available have a relatively short post exposure delay (PED) stability. In general, when there is delay between exposure of the photoresist to light and development of the exposed photoresist, acids that are generated on the exposed area are neutralized by amine compounds which may be present in the production atmosphere. Since the pattern formation depends on acids that are generated by the exposure, neutralization of acids by atmospheric amine compounds reduce, prevent or alter a pattern formation, e.g., a T-topping phenomenon may occur where the top portion of the pattern forms a T-shape.

Therefore, there is a need for a photoresist polymer having an excellent etching properties, heat resistance and enhanced PED stability.

SUMMARY OF THE INVENTION

An object of the present invention is to provide a novel PR polymer having an excellent etching and heat resistance, and an enhanced PED stability. The present inventors have found that a polymer derived from a monomer comprising a bicyclo compound achieves such an objective.

Another object of the present invention is to provide PR polymers using the PR monomers described above and a process for preparing the same.

Yet another object of the present invention is to provide photoresist compositions using the PR polymers described above, and a process for preparing the same.

Still another object of the present invention is to provide a semiconductor device produced by using the PR composition described above.

DETAILED DESCRIPTION OF THE INVENTION

The present invention provides a bicyclic PR monomers represented by following formula:

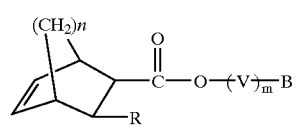

1 where B is selected from the group consisting of moieties of the formula:

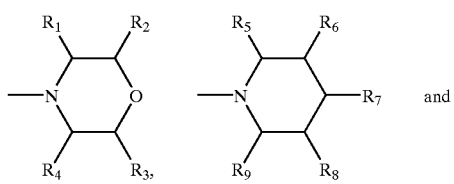 and

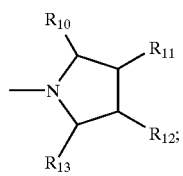

R is hydrogen, substituted or non-substituted ($C_1$–$C_{10}$) straight or branched chain alkyl, cycloalkyl, alkoxyalkyl, cycloalkoxyalkyl, —COOR', —($CH_2$)$_t$OH, —COO($CH_2$)$_t$OH or a moiety of the formula:

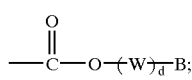

R' is hydrogen, substituted or non-substituted ($C_1$–$C_{10}$) straight or branched chain alkyl, cycloalkyl, alkoxyalkyl or cycloalkoxyalkyl;

each of V and W is independently substituted or non-substituted ($C_1$–$C_{10}$) straight or branched chain alkylene, cycloalkylene, alkoxyalkylene or cycloalkoxyalkylene;

each of $R_1$–$R_{13}$ is independently hydrogen, substituted or non-substituted ($C_1$–$C_{10}$) straight or branched chain alkyl, cycloalkyl, alkoxyalkyl, cycloalkoxyalkyl, —$CH_2$OH or —$CH_2CH_2$OH;

n is an integer from 1 to 3; and each of d, m and t is independently an integer from 0 to 5.

Particularly preferred bicyclo PR monomers of the present invention are:

(morpholin-4-yl)ethyl 5-norbornene-2-carboxylate:

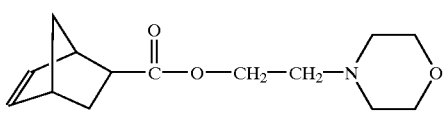

1a 2-(morpholin-4-yl)ethyl 5-norbornene-2,3-dicarboxylate:

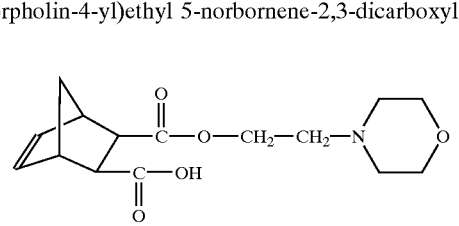

1b 2-(morpholin-4-yl)ethyl, 3-tert-butyl 5-norbornene-2,3-dicarboxylate:

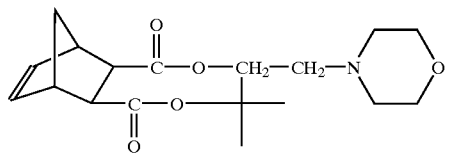

1c 2,3-di[(morpholin-4-yl)ethyl]5-norbornene-2,3-dicarboxylate:

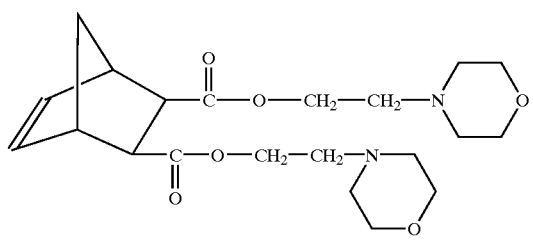

(piperidin-1-yl)ethyl 5-norbornene-2-carboxylate:

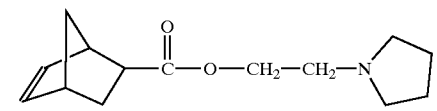

1e (pyrrolidin-1-yl)ethyl 5-norbornene-2-carboxylate:

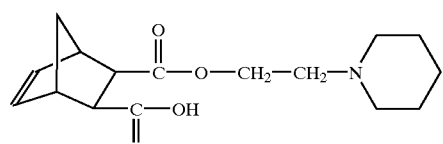

1f 2-(piperidin-1-yl)ethyl 5-norbornene-2,3-dicarboxylate:

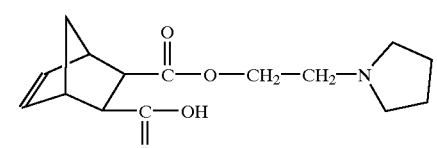

1g 2-(pyrrolidin-1-yl)ethyl 5-norbornene-2,3-dicarboxylate:

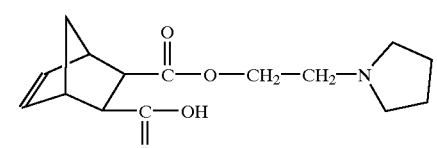

1h 2-(piperidin-1-yl)ethyl, 3-tert-butyl 5-norbornene-2,3-dicarboxylate:

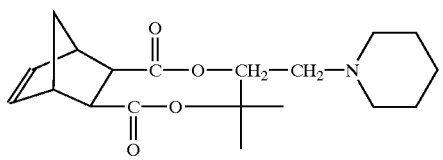

2-(pyrrolidin-1-yl)ethyl, 3-tert-butyl 5-norbornene-2,3-dicarboxylate:

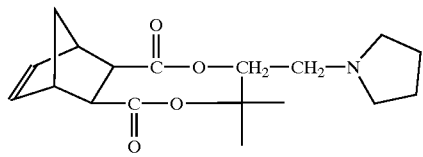

2,3-di[(piperidin-1-yl)ethyl]5-norbornene-2,3-dicarboxylate:

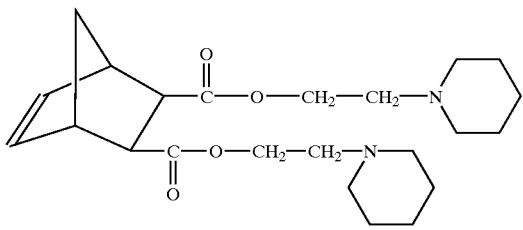

2,3-di[(pyrrolidin-1-yl)ethyl]5-norbornene-2,3-dicarboxylate:

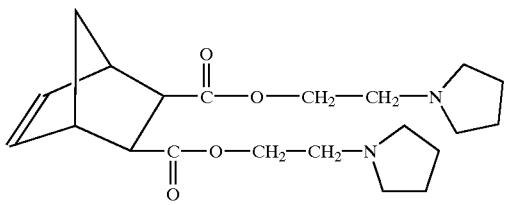

The compound represented by Chemical Formula 1 can be prepared by a variety of methods. In one method of preparing compounds of formula 1, which is particularly useful for compounds of formula 1, where R is hydrogen or substituted or non-substituted ($C_1$–$C_{10}$) straight or branched chain alkyl, cycloalkyl, alkoxyalkyl or cycloalkoxyalkyl, the method comprises:

(a1) reacting a diene compound of the formula:

with an acrylate of the formula:

$$CH\!\!=\!\!CHCOOH$$
$$|$$
$$R$$

to produce a bicyclic carboxylic acid of the formula:

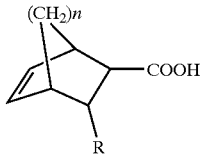

where R is hydrogen or substituted or non-substituted ($C_1$–$C_{10}$) straight or branched chain alkyl, cycloalkyl, alkoxyalkyl or cycloalkoxyalkyl; and n is an integer from 1 to 3;

(b1) reacting the bicyclic carboxylic acid 4 with thionyl chloride ($SOCl_2$), preferably in an equal molar amount; and (c1) reacting the product of step (b1) with a hydroxy compound of the formula:

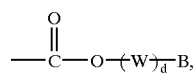

to produce the desired compound 1, where B, V and m are those defined above.

In one particular method of the present invention, compound 2 is dissolved in an organic solvent and cooled to temperature in the range of from about –35° C. to about –25° C., and compound 3 is slowly added to the mixture. The resulting reaction mixture is stirred for about 8 to 12 hours at temperature in the range of from about –35° C. to about –25° C. After which the reaction temperature is allowed to reach room temperature. The resulting mixture is stirred for additional about 8 to 12 hours. Compound 4 can be recovered by a standard work-up followed by concentration of the resulting organic phase.

In the step (c1) above, triethylamine, preferably in an equal molar amount, is added to the reaction mixture to neutralize any acids that is formed in the reaction mixture. An aqueous work-up followed by drying the organic phase, filtering, and removing the organic solvent, e.g., by vacuum distillation, provides the desired compound.

In another method of preparing compounds of formula 1, which is particularly useful for compounds of formula 1, where R is COOR' or

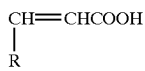

the method comprises:

(a2) reacting a diene compound of formula 2 with maleic anhydride to produce 5-norbornene-2,3-dicarboxylic anhydride;

(b2) (i) when R is COOR', contacting said 5-norbornene-2,3-dicarboxylic anhydride with R'OH in the presence of an acid catalyst to produce a 5-norbornene-2,3- dicarboxylate compound; or (ii) when R is

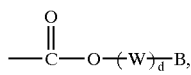

hydrolyzing the 5-norbornene-2,3-dicarboxylic anhydride to produce a 5-norbornene-2,3-dicarboxylic acid; and (c2) reacting the 5-norbornene-2,3-dicarboxylate compound or 5-norbornene-2,3-dicarboxylic acid with a hydroxy compound of formula 5 to produce the desired compound 1, where B, W, R' and d are those defined above.

More specifically, in the step (a2) above, compound 2 is dissolved in an organic solvent and cooled at temperature in the range of from about −35° C. to about −25° C. Maleic anhydride, preferably in a solution and in an equal amount, is slowly added to the resulting solution. The reaction mixture is then stirred for about 8 to 12 hours at temperature in the range of from about −35° C. to about −25° C. After which the reaction temperature is allowed to reach room temperature. The reaction mixture is stirred for additional about 8 to 12 hours, and the 5-norbornene-2,3-dicarboxylic anhydride is obtained after removing the organic solvent.

And, when the R is

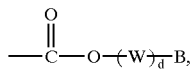

the step of (c2) comprises reacting the hydroxy compound 5, preferably in an amount which is double the theoretical amount (in moles) of the 5-norbornene-2,3-dicarboxylate compound, in the presence of triethylamine, preferably in the amount equal to the amount of the hydroxy compound 5. Aqueous work-up followed by drying the organic phase, filtering and concentrating, e.g., by vacuum distillation, then provides the desired compound of formula 1.

While any non-protic organic solvent can be used in the steps (a1) or (a2) above, preferred organic solvents include tetrahydrofuran (THF), dimethylformamide, dimethylsulfoxide, dioxane, benzene, toluene and xylene.

The present invention also provides a PR copolymers which is derived from a monomer comprising the compound of formula 1. The PR copolymer according to the present invention can further comprise a second monomer selected from the group consisting of compounds of the formulas:

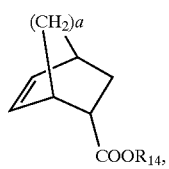

6

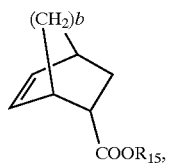

7

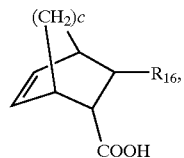

8 and mixtures thereof; where $R_{14}$ is substituted or non-substituted ($C_1$–$C_{10}$) straight or branched chain alcohol; $R_{15}$ is an acid labile protecting group; $R_{16}$ is hydrogen or —COOH; and a, b, and c are independently an integer from 1 to 3.

The copolymer of the present invention can further comprise maleic anhydride as a third monomer.

Preferably, the PR copolymer of the present invention has a molecular weight in the range of from about 3000 to about 100,000. Particularly preferred PR copolymers of the present invention include:

poly(tert-butyl 5-norbornene-2-carboxylate/2-hydroxyethyl 5-norbornene-2-carboxylate/5-norbornene-2-carboxylic acid/2-(morpholin-4-yl)ethyl 5-norbornene-2-carboxylate/maleic anhydride):

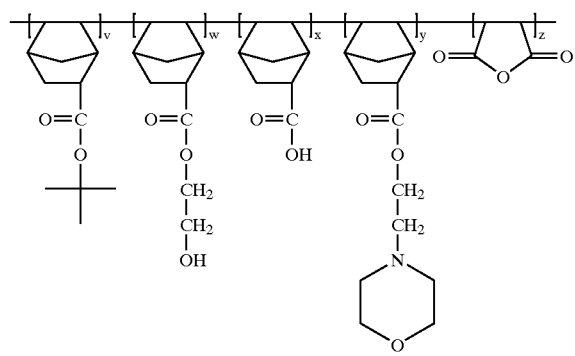

9a poly(tert-butyl 5-norbornene-2-carboxylate/2-hydroxyethyl 5-norbornene-2-carboxylate/5-norbornene-2-carboxylic acid/2-(morpholin-4-yl)ethyl 5-norbornene-2,3-dicarboxylate/maleic anhydride):

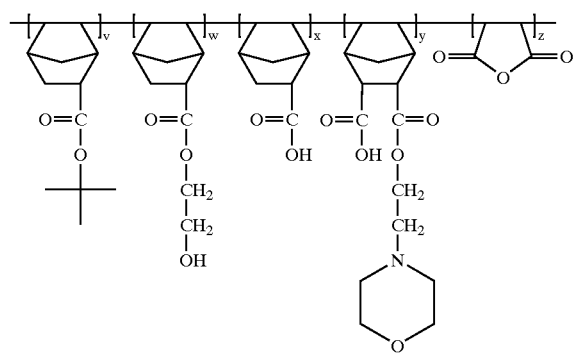

9b poly(tert-butyl 5-norbornene-2-carboxylate/2-hydroxyethyl 5-norbornene-2-carboxylate/5-norbornene-2-carboxylic acid/2-(morphlin-4-yl)ethyl, 3-tert-butyl 5-norbornene-2,3-dicarboxylate/maleic anhydride):

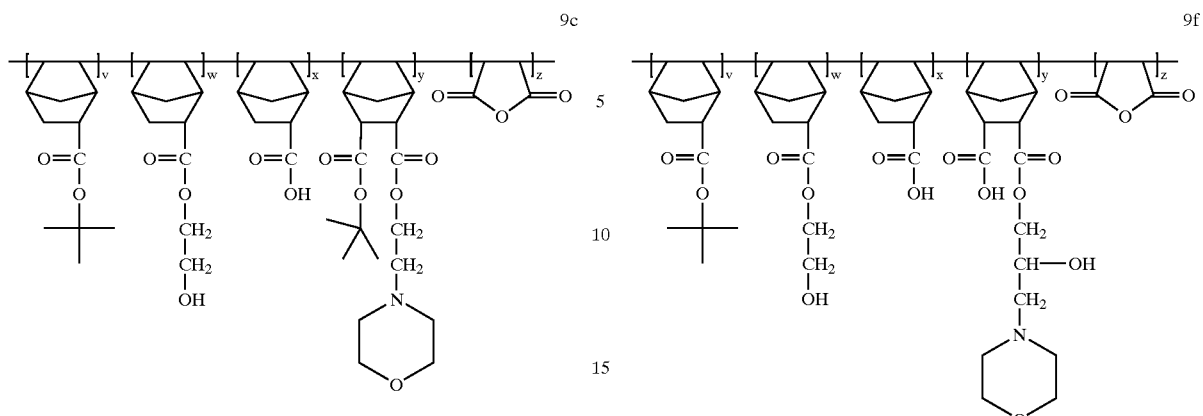

poly(tert-butyl 5-norbornene-2-carboxylate/2-hydroxyethyl 5-norbornene-2-carboxylate/5-norbornene-2-carboxylic acid/2,3-di[2-(morpholin-4-yl)ethyl]5-norbornene-2,3-dicarboxylate/maleic anhydride):

poly(tert-butyl 5-norbornene-2-carboxylate/2-hydroxyethyl 5-norbornene-2-carboxylate/5-norbornene-2-carboxylic acid/3-(morpholin-4-yl)-2-hydroxypropyl 5-norbornene-2-carboxylate/maleic anhydride:

poly(tert-butyl 5-norbornene-2-carboxylate/2-hydroxyethyl 5-norbornene-2-carboxylate/5-norbornene-2-carboxylic acid/2-[3-(morpholin-4-yl)-2-hydroxypropyl]5-norbornene-2,3-dicarboxylate/maleic anhydride):

poly(tert-butyl 5-norbornene-2-carboxylate/2-hydroxyethyl 5-norbornene-2-carboxylate/5-norbornene-2-carboxylic acid/2-[3-(morpholin-4-yl)-2-hydroxypropyl], 3-tert-butyl 5-norbornene-2,3-dicarboxylate/maleic anhydride):

poly(tert-butyl 5-norbornene-2-carboxylate/2-hydroxyethyl 5-norbornene-2-carboxylate/5-norbornene-2-carboxylic acid/2,3-di[3-(morpholin-4-yl)-2-hydroxypropyl]5-norbornene-2,3-dicarboxylate/maleic anhydride):

poly(tert-butyl 5-norbornene-2-carboxylate/2-hydroxyethyl 5-norbornene-2-carboxylate/5- norbornene-2-carboxylic acid/2-(piperidin-1-yl)ethyl 5-norbornene-2-carboxylate/maleic anhydride):

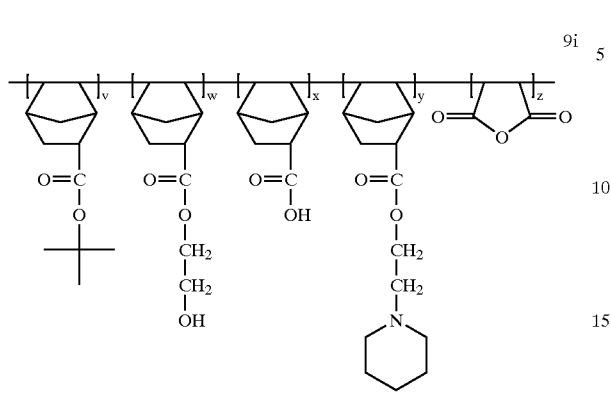

poly(tert-butyl 5-norbornene-2-carboxylate/2-hydroxyethyl 5-norbornene-2-carboxylate/5-norbornene-2-carboxylic acid/2-(pyrrolidin-1-yl)ethyl 5-norbornene-2-carboxylate/maleic anhydride):

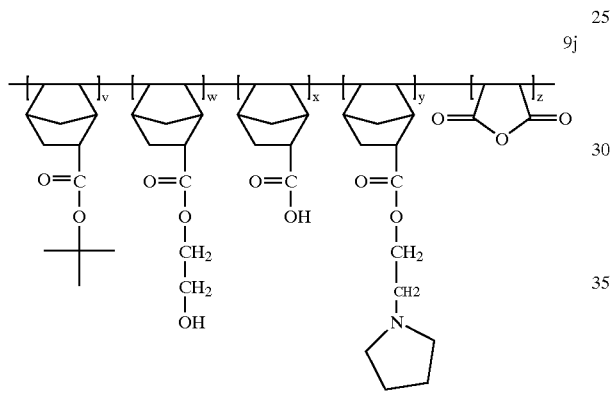

poly(tert-butyl 5-norbornene-2-carboxylate/2-hydroxyethyl 5-norbornene-2-carboxylate/5-norbornene-2-carboxylic acid/2-(piperidin-1-yl)ethyl 5-norbornene-2,3-dicarboxylate/maleic anhydride):

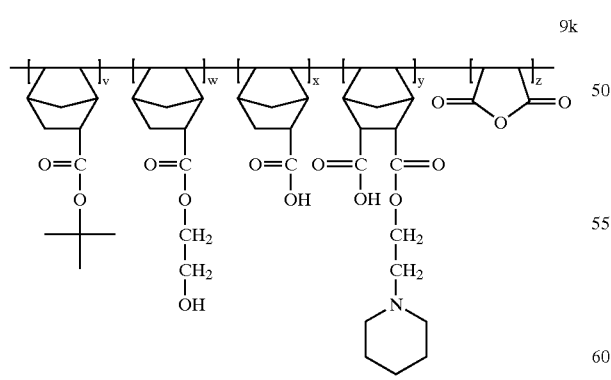

poly(tert-butyl 5-norbornene-2-carboxylate/2-hydroxyethyl 5-norbornene-2-carboxylate/5-norbornene-2-carboxylic acid/2-(pyrrolidin-1-yl)ethyl 5-norbornene-2,3-dicarboxylate/maleic anhydride):

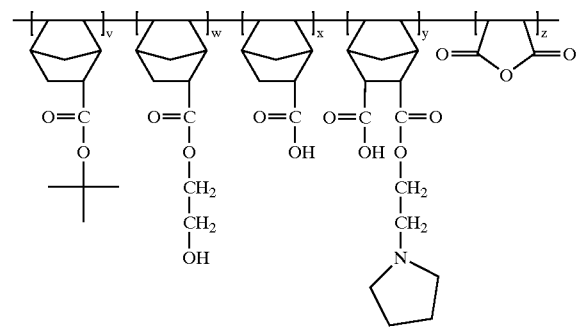

poly(tert-butyl 5-norbornene-2-carboxylate/2-hydroxyethyl 5-norbornene-2-carboxylate/5-norbornene-2-carboxylic acid/2-(piperidin-1-yl)ethyl, 3-tert-butyl 5-norbornene-2,3-dicarboxylate/maleic anhydride):

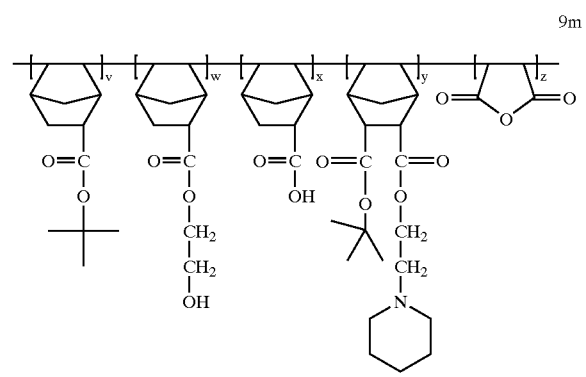

poly(tert-butyl 5-norbornene-2-carboxylate/2-hydroxyethyl 5-norbornene-2-carboxylate/5-norbornene-2-carboxylic acid/2-(pyrrolidin-1-yl)ethyl, 3-tert-butyl 5-norbornene-2,3-dicarboxylate/maleic anhydride):

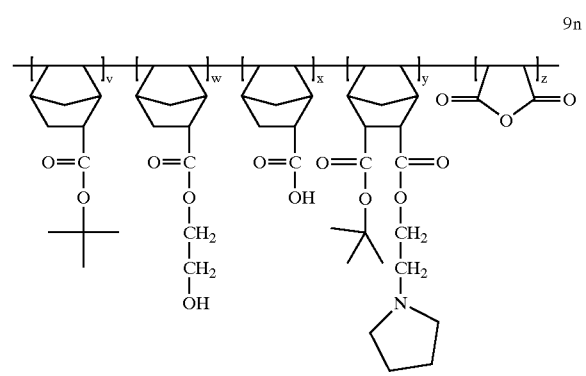

poly(tert-butyl 5-norbornene-2-carboxylate/2-hydroxyethyl 5-norbornene-2-carboxylate/5-norbornene-2-carboxylic acid/2,3-di[2-(piperidin-1-yl)ethyl]5-norbornene-2,3-dicarboxylate/maleic anhydride):

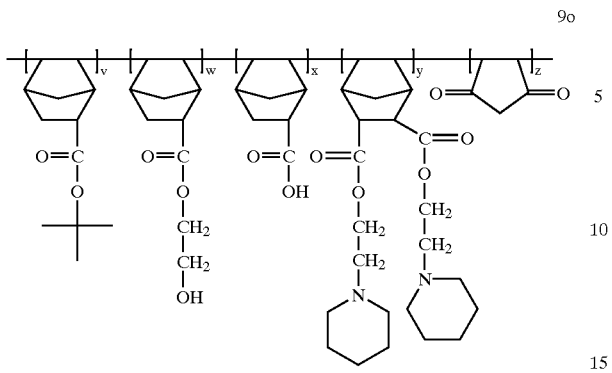

9o poly(tert-butyl 5-norbornene-2-carboxylate/2-hydroxyethyl 5-norbornene-2-carboxylate/5-norbornene-2-carboxylic acid/2,3-di[2-(pyrrolidin-1-yl)ethyl]5-norbornene-2,3-dicarboxylate/maleic anhydride):

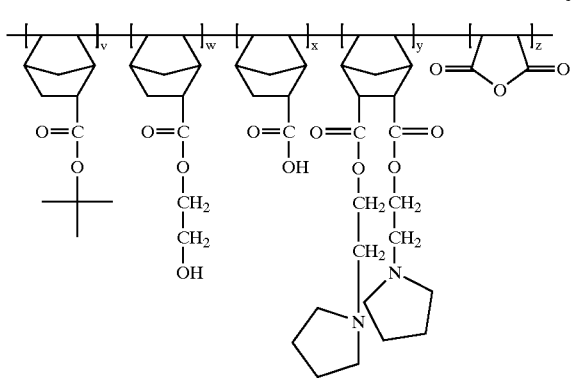

9p poly(tert-butyl 5-norbornene-2-carboxylate/2-hydroxyethyl 5-norbornene-2-carboxylate/5-norbornene-2,3-dicarboxylic acid/2,3-di[2-(piperidin-1-yl)ethyl]5-norbornene-2,3-dicarboxylate/maleic anhydride):

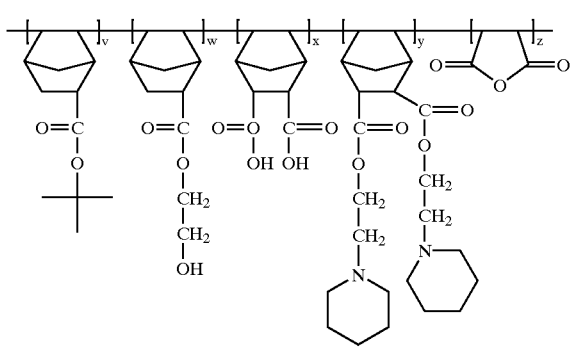

9q poly(tert-butyl 5-norbornene-2-carboxylate/2-hydroxyethyl 5-norbornene-2-carboxylate/5-norbornene-2,3-dicarboxylic acid/2,3-di[2-(pyrrolidin-1-yl)ethyl]5-norbornene-2,3-dicarboxylate/maleic anhydride):

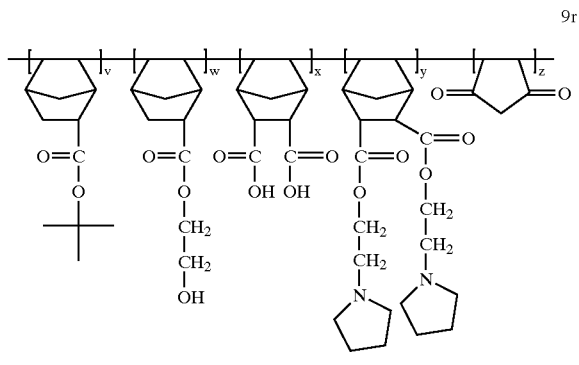

9r

In the above Formulas 9a to 9r, the ratio of v:w:x:y:z is preferably 0.01 to 99 mol %: 0.01 to 99 mol %: 0.01 to 35 mol %: 0.01 to 35 mol %: 0.01 to 99 mol %.

The copolymer of the present invention can be prepared by radical polymerization of monomers with a conventional radical polymerization initiator. An exemplary procedure for preparing copolymers of the present invention includes the steps of:

(a) admixing
  (i) a compound of formula 1,
  (ii) a second monomer selected from the group consisting of compounds of formulas 6, 7, 8, and mixtures thereof,
  (iii) optionally maleic anhydride, and
  (iv) a polymerization initiator; in an organic solvent; and (b) polymerizing the admixture under an inert atmosphere, preferably under nitrogen or argon atmosphere.

The polymerization can be carried out by either a bulk polymerization or a solution polymerization. Exemplary solvents suitable for polymerization include cyclohexanone, tetrahydrofuran, dimethylformamide, dimethylsulfoxide, dioxane, methyl ethyl ketone, benzene, toluene and xylene.

Exemplary polymerization initiators include any conventional radical polymerization initiators such as benzoylperoxide, 2,2'-azobisisobutyronitile (AIBN), acetylperoxide, laurylperoxide, tert-butylperacetate, tert-butylhydroperoxide and di-tert-butylperoxide. Preferred polymerization temperature is in the range of from about 40° C. to about 90° C., and a preferred polymerization reaction time is in the range of from about 4 hours to about 20 hours.

The present invention also provides a PR composition comprising the PR copolymer of the present invention, an organic solvent, and a photoacid generator.

Preferred photoacid generators include sulfides and onium type compounds. In one particular embodiment of the present invention, the photoacid generator is selected from the group consisting of diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluororphosphate, triphenylsulfonium hexafluoroarsenate, triphenylsulfonium hexafluoroantimonate, triphenylsulfonium triflate and dibutylnaphthylsulfonium triflate. Typically, the amount of photoacid generator used is from about 0.05% by weight to about 10% by weight of the photoresist resin (i.e., PR copolymer) employed. It has been found that when the photoacid generator is used in the amount less than about 0.05%, photosensitivity of the PR composition is decreased. And when the photoacid generator is used in the amount greater than about 10%, a poor patterning results due to its large absorption of DUV (Deep Ultra Violet).

Exemplary organic solvents suitable in PR compositions of the present invention include methyl 3-methoxypropionate, ethyl 3-ethoxypriopionate, propylene glycol methyl ether acetate, cyclohexanone, 2-heptanone and (2-methoxy)ethyl acetate. The amount of solvent used is preferably in the range of from about 200% to about 1000% by weight of the PR resin. This ratio has been found to be particularly useful in obtaining a photoresist layer of desirable thickness when coated on to a suitable substrate such as a silicon wafer in production of a semiconductor element. In particular, it has been found by the present inventors that when the amount of organic solvent is about 600% by weight of the PR copolymer, a PR layer having 0.45 µm of thickness may be obtained.

The PR composition is prepared by dissolving the PR copolymer of the present invention in an organic solvent in the amount of about 10% to about 30% by weight of the solvent, adding the photoacid generator in the amount of from about 0.05% to about 10% by weight of the copolymer, and filtering the resulting composition through a hyperfine filter.

The PR composition prepared by the present invention has an excellent etching resistance, adhesiveness and heat resistance. Also, its remarkably enhanced PED stability makes it very useful as an ArF photosensitive film.

The present invention also provides a method for forming a PR pattern as follows: (a) coating the above described photoresist composition on a substrate of semiconductor element to form a photoresist film; (b) exposing the photoresist film to light using a light source; and (c) developing the photoresist film, for example, using an alkaline solution such as 2.38 wt % TMAH solution. Optionally, the photoresist film can be heated (i.e., baked), preferably to temperature in the range of from about 70° C. to about 200° C., before and/or after the step (b).

Exemplary light sources which are useful for forming a PR pattern include ArF (193 nm), KrF (248 nm), VUV (157 nm), EUV, E-beam, X-ray and ion beam. Preferably, the irradiation energy is in the range of from about 1 mJ/cm$^2$ to about 100 mJ/cm$^2$.

The present invention also provides a semiconductor device, which is manufactured using the photoresist composition described above.

Additional objects, advantages, and novel features of this invention will become apparent to those skilled in the art upon examination of the following examples thereof, which are not intended to be limiting.

Preparation of the Photoresist Monomers

EXAMPLE 1

Synthesis of 2-(morpholin-4-yl)ethyl 5-norbornene-2-carboxylate

Cyclopentadiene, which was obtained by thermolysis of dicyclopentadiene, was dissolved in a conventional organic solvent, and the solution was cooled to about −30° C. About 1 equiv. of cooled acryl acid was slowly added to the solution. The reaction mixture was stirred for about 10 hours, after which the reaction mixture was allowed to reach room temperature and stirred for additional 10 hours. The solvent was removed using a rotary evaporator, and 5-norbornene-2-carboxylic acid was obtained by vacuum distillation. About 1 mole of 5-norbornene-2-carboxylic acid and about 1 mole of thionyl chloride were slowly combined and agitated in a bath. The remaining or unreacted thionyl chloride was removed and about 1 mole of triethylamine and 4-(2-hydroxyethyl)morpholine were added to the mixture. The reaction mixture was extracted with ethyl acetate. And the organic layer was separated, dried over anhydrous MgSO$_4$, and concentrated to provide the title compound represented by formula 1a in 75% yield.

EXAMPLE 2

Synthesis of 2-(morpholin-4-yl)ethyl 5-norbornene-2,3-dicarboxylate

Using the procedure of Example 1, cyclopentadiene was reacted with maleic anhydride to provide 5-norbornene-2,3-dicarboxylic anhydride, which was then slowly added to a 10% NaOH aqueous solution. The resulting mixture was heated to about 85° C. for about 90 minutes and slowly cooled to room temperature. The resulting solution was neutralized by adding 10% sulfuric acid drop-wise. The reaction mixture was extracted using ethyl acetate. The organic phase was separated, dried over anhydrous MgSO$_4$, filtered, and concentrated to yield 5-norbornene-2,3-dicarboxylic acid as a white solid.

About 1 mole of 5-norbornene-2,3-dicarboxylic acid and about 1 mole of thionyl chloride were combined and slowly agitated in a bath. After the reaction was complete, the remaining or unreacted thionyl chloride was removed and 1 mole of triethylamine and 1 mole of 4-(2-hydroxyethyl)morpholine were added to the reaction mixture. The reaction mixture was quenched and extracted with ethyl acetate. The organic phase was separated, dried over anhydrous MgSO$_4$, filtered, and concentrated to provide the title compound represented by formula 1b in 70% yield.

EXAMPLE 3

Synthesis of 2-(morpholin-4-yl)ethyl, 3-tert-butyl 5-norbornene-2,3-dicarboxylate 5-Norbornene-2,3-dicarboxylic anhydride was obtained using the procedure of Example 2. About 1 mole of 5-norbornene-2,3-dicarboxylic anhydride and about 1 mole of tert-butanol were slowly combined and stirred in the presence of an acid catalyst. The resulting mixture was refluxed at about 60° C. for about 5 hours, and slowly cooled to room temperature. The reaction mixture was quenched and extracted with ethyl acetate. The organic phase was separated, dried over anhydrous MgSO$_4$, filtered, and concentrated to provide tert-butyl 5-norbornene-2,3-dicarboxylate as a white solid.

About 1 mole of tert-butyl 5-norbornene-2,3-dicarboxylate and about 1 mole of thionyl chloride were combined and slowly agitated in a bath. After the reaction was completed, the remaining thionyl chloride was removed and 1 mole of triethylamine and 1 mole of the 4-(2-hydroxyethyl)morpholine were added to the reaction mixture. The reaction was quenched and extracted with ethyl acetate. The organic phase was separated, dried over anhydrous MgSO$_4$, filtered, and concentrated to provide the compound of formula 1c in 72% yield.

EXAMPLE 4

Synthesis of 2,3-di[2-(morpholin-4-yl)ethyl]5-norbornene-2,3-dicarboxylate

Using the procedure of Example 2, maleic anhydride and cyclopentadiene were reacted to produce 5-norbornene-2,3-dicarboxylic acid as a white solid. About 1 mole of 5-norbornene-2,3-dicarboxylic acid and about 2 moles of thionyl chloride were slowly agitated in a bath. Upon the completion of the reaction, the remaining thionyl chloride was removed and 2 moles of triethylamine and 2 moles of 4-(2-hydroxyethyl)morpholine were added. Work-up followed by concentration as described in Example 2 gave the title compound of formula 1d in 67% yield.

EXAMPLE 5
Synthesis of 2-(piperidin-1-yl)ethyl-5-norbornene-2-carboxylate

The procedure of Example 1 is repeated except for using 1 mole of 1-(2-hydroxyethyl)piperidine instead of 1 mole of 4-(2-hydroxyethyl)morpholine to obtain the title compound of formula 1e in 78% yield.

EXAMPLE 6
Synthesis of 2-(pyrrolidin-1-yl)ethyl 5-norbornene-2-carboxylate

The procedure of Example 1 is repeated except for using 1 mole of 1-(2-hydroxyethyl)pyrrolidine instead of 1 mole of 4-(2-hydroxyethyl)morpholine to obtain the title compound of formula 1f in 75% yield.

EXAMPLE 7
Synthesis of 2-(piperidin-1-yl)ethyl 5-norbornene-2,3-dicarboxylate The procedure of Example 2 is repeated except for using 1 mole of 1-(2-hydroxyethyl)piperidine instead of 1 mole of 4-(2-hydroxyethyl)morpholine to obtain the title compound of formula 1g in 71% yield.

EXAMPLE 8
Synthesis of 2-(pyrrolidin-1-yl)ethyl 5-norbornene-2,3-dicarboxylate The procedure of Example 2 is repeated except for using 1 mole of 1-(2-hydroxyethyl)pyrrolidine instead of 1 mole of 4-(2-hydroxyethyl)morpholine to obtain the title compound of formula 1h in 70% yield.

EXAMPLE 9
Synthesis of 2-(piperidin-1-yl)ethyl, 3-tert-butyl 5-norbornene-2,3-dicarboxylate The procedure of Example 3 is repeated except for using 1 mole of 1-(2-hydroxyethyl)piperidine instead of 1 mole of 4-(2-hydroxyethyl)morpholine to obtain the title compound of formula 1i in 70% yield.

EXAMPLE 10
Synthesis of 2-(pyrrolidin-1-yl)ethyl, 3-tert-butyl 5-norbornene-2,3-dicarboxylate The procedure of Example 3 is repeated except for using 1 mole of 1-(2-hydroxyethyl)pyrrolidine instead of 1 mole of 4-(2-hydroxyethyl)morpholine to obtain the title compound of formula 1j in 71% yield.

EXAMPLE 11
Synthesis of 2,3-di[2-(piperidin-1-yl)ethyl]5-norbornene-2,3-dicarboxylate The procedure of Example 4 is repeated except for using 2 mole of 1-(2-hydroxyethyl)piperidine instead of 2 mole of 4-(2-hydroxyethyl)morpholine to obtain the title compound of formula 1k in 68% yield.

EXAMPLE 12
Synthesis of 2,3-di[2-(pyrrolidin-1-yl)ethyl]5-norbornene-2,3-dicarboxylate The procedure of Example 4 is repeated except for using 2 mole of 1-(2-hydroxyethyl)pyrrolidine instead of 2 mole of 4-(2-hydroxyethyl)morpholine to obtain the title compound of formula 1l in 67% yield.

Preparation of the Photoresist Polymers

EXAMPLE 13
Synthesis of poly(tert-butyl 5-norbornene-2-carboxylate/2-hydroxyethyl 5-norbornene-2-carboxylate/5-norbornene-2-carboxylic acid/2-(morpholin-4-yl)ethyl 5-norbornene-2-carboxylate/maleic anhydride)

0.80 mole of tert-butyl 5-norbornene-2-carboxylate, 0.1 mole of 2-hydroxyethyl 5-norbornene-2-carboxylate, 0.05 mole of 5-norbornene-2-carboxylic acid, 0.05 mole of (morpholin-4-yl)ethyl 5-norbornene-2-carboxylate and 1 mole of maleic anhydride were dissolved in a solvent such as THF. Then, 5.5 g of polymerization initiator, AIBN, was added to the resulting solution and the polymerization was carried out under an Argon atmosphere at temperature of about 67° C. for about 10 hours. After which the reaction mixture was precipitated using ethyl ether, and the precipitate was collected and vacuum dried to provide the title copolymer compound of formula 9a in 34% yield.

EXAMPLE 14
Synthesis of poly(tert-butyl 5-norbornene-2-carboxylate/2-hydroxyethyl 5-norbornene-2-carboxylate/5-norbornene-2-carboxylic acid/2-(morpholin-4-yl)ethyl 5-norbornene-2,3-dicarboxylate/maleic anhydride)

The procedure of Example 13 was repeated except for using 0.05 mole of 2-(morpholin-4-yl)ethyl 5-norbornene-2,3-dicarboxylate instead of 0.05 mole of 2-(morpholin-4-yl)ethyl 5-norbornene-2-carboxylate to obtain the title compound of formula 9b in 31% yield.

EXAMPLE 15
Synthesis of poly(tert-butyl 5-norbornene-2-carboxylate/2-hydroxyethyl 5-norbornene-2-carboxylate/5-norbornene-2-carboxylic acid/2-(morpholin-4-yl)ethyl, 3-tert-butyl 5-norbornene-2,3-dicarboxylate/maleic anhydride)

The procedure of Example 13 was repeated except for using 0.05 mole of 2-(morpholin-4-yl)ethyl, 3-tert-butyl 5-norbornene-2,3-dicarboxylate instead of 0.05 mole of (morpholin-4-yl)ethyl 5-norbornene-2-carboxylate to obtain the title compound of formula 9c in 33% yield.

EXAMPLE 16
Synthesis of poly(tert-butyl 5-norbornene-2-carboxylate/2-hydroxyethyl 5-norbornene-2-carboxylate/5-norbornene-2-carboxylic acid/2,3-di[2-(morpholin-4-yl)ethyl]5-norbornene-2,3-dicarboxylate/maleic anhydride)

The procedure of Example 13 was repeated except for using 0.05 mole of 2,3-di[2-(morpholin-4-yl)ethyl]5-norbornene-2,3-dicarboxylate instead of 0.05 mole of 2-(morpholin-4-yl)ethyl 5-norbornene-2-carboxylate to obtain the title compound of formula 9d in 30% yield.

EXAMPLE 17
Synthesis of poly(tert-butyl 5-norbornene-2-carboxylate/2-hydroxyethyl 5-norbornene-2-carboxylate/5-norbornene-2-carboxylic acid/3-(morpholin-4-yl)-2-hydroxypropyl 5-norbornene-2-carboxylate/maleic anhydride)

The procedure of Example 13 was repeated except for using 0.05 mole of 3-(morpholin-4-yl)-2-hydroxypropyl 5-norbornene-2-carboxylate instead of 0.05 mole of 2-(morpholin-4-yl)ethyl 5-norbornene-2-carboxylate to obtain the title compound of formula 9e in 33% yield.

EXAMPLE 18
Synthesis of poly(tert-butyl 5-norbornene-2-carboxylate/2-hydroxyethyl 5-norbornene-2-carboxylate/5-norbornene-2-carboxylic acid/2-[(3-morpholin-4-yl)-2-hydroxypropyl]5-norbornene-2,3-dicarboxylate/maleic anhydride)

The procedure of Example 13 was repeated except for using 0.05 mole of 2-[(3-morpholin-4-yl)-2-hydroxypropyl] 5-norbornene-2,3-dicarboxylate instead of 0.05 mole of 2-(morpholin-4-yl)ethyl 5-norbornene-2-carboxylate to obtain the title compound of formula 9f in 32% yield.

EXAMPLE 19
Synthesis of poly(tert-butyl 5-norbornene-2-carboxylate/2-hydroxyethyl 5-norbornene-2-carboxylate/5-norbornene-2-carboxylic acid/2-[(3-morpholin-4-yl)-2-hydroxypropyl], 3-tert-butyl 5-norbornene-2,3-dicarboxylate/maleic anhydride)

The procedure of Example 13 was repeated except for using 0.05 mole of 2-[(3-morpholin-4-yl)-2-hydroxypropyl], 3-tert-butyl 5-norbornene-2,3-dicarboxylate instead of 0.05 mole of 2-(morpholin-4-yl) ethyl 5-norbornene-2-carboxylate to obtain the title compound of formula 9g in 32% yield.

EXAMPLE 20
Synthesis of poly(tert-butyl 5-norbornene-2-carboxylate/2-hydroxyethyl 5-norbornene-2-carboxylate/5-norbornene-2-carboxylic acid/2,3-di[(3-morpholin-4-yl-2-hydroxypropyl] 5-norbornene-2,3-dicarboxylate/maleic anhydride)

The procedure of Example 13 was repeated except for using 0.05 mole of 2,3-di[(3-morpholin-4-yl)-2-hydroxypropyl]5-norbornene-2,3-dicarboxylate instead of 0.05 mole of 2-(morpholin-4-yl)ethyl 5-norbornene-2-carboxylate to obtain the title compound of formula 9h in 30% yield.

EXAMPLE 21
Synthesis of poly(tert-butyl 5-norbornene-2-carboxylate/2-hydroxyethyl 5-norbornene-2-carboxylate/5-norbornene-2-carboxylic acid/2-(piperidin-1-yl)ethyl 5-norbornene-2-carboxylate/maleic anhydride)

The procedure of Example 13 was repeated except for using 0.05 mole of 2-(piperidin-1-yl)ethyl 5-norbornene-2-carboxylate instead of 0.05 mole of 2-(morpholin-4-yl)ethyl 5-norbornene-2-carboxylate to obtain the title compound of formula 9i in 33% Yield.

EXAMPLE 22
Synthesis of poly(tert-butyl 5-norbornene-2-carboxylate/2-hydroxyethyl 5-norbornene-2-carboxylate/5-norbornene-2-carboxylic acid/2-(pyrrolidin-1-yl)ethyl 5-norbornene-2-carboxylate/maleic anhydride)

The procedure of Example 13 was repeated except for using 0.05 mole of 2-(pyrrolidin-1-yl)ethyl 5-norbornene-2-carboxylate instead of 0.05 mole of 2-(morpholin-4-yl)ethyl 5-norbornene-2-carboxylate to obtain the title compound of formula 9j in 32% yield.

EXAMPLE 23
Synthesis of poly(tert-butyl 5-norbornene-2-carboxylate/2-hydroxyethyl 5-norbornene-2-carboxylate/5-norbornene-2-carboxylic acid/2-(piperidin-1-yl)ethyl 5-norbornene-2,3-dicarboxylate/maleic anhydride)

The procedure of Example 13 was repeated except for using 0.05 mole of 2-(piperidin-1-yl)ethyl 5-norbornene-2,3-dicarboxylate instead of 0.05 mole of 2-(morpholin-4-yl) ethyl 5-norbornene-2-carboxylate to obtain the title compound of formula 9k in 30% yield.

EXAMPLE 24
Synthesis of poly(tert-butyl 5-norbornene-2-carboxylate/2-hydroxyethyl 5-norbornene-2-carboxylate/5-norbornene-2-carboxylic acid/2-(pyrrolidin-1-yl)ethyl 5-norbornene-2,3-dicarboxylate/maleic anhydride)

The procedure of Example 13 was repeated except for using 0.05 mole of 2-(pyrrolidin-1-yl)ethyl 5-norbornene-2,3-dicarboxylate instead of 0.05 mole of 2-(morpholin-4-yl) ethyl 5-norbornene-2-carboxylate to obtain the title compound of formula 9l in 33% yield.

EXAMPLE 25
Synthesis of poly(tert-butyl 5-norbornene-2-carboxylate/2-hydroxyethyl 5-norbornene-2-carboxylate/5-norbornene-2-carboxylic acid/2-(piperidin-1-yl)ethyl, 3-tert-butyl 5-norbornene-2,3-dicarboxylate/maleic anhydride)

The procedure of Example 13 was repeated except for using 0.05 mole of 2-(piperidin-1-yl)ethyl, 3-tert-butyl 5-norbornene-2,3-dicarboxylate instead of 0.05 mole of 2-(morpholin-4-yl)ethyl 5-norbornene-2-carboxylate to obtain the title compound of formula 9m in 34% yield.

EXAMPLE 26
Synthesis of poly(tert-butyl 5-norbornene-2-carboxylate/2-hydroxyethyl 5-norbornene-2-carboxylate/5-norbornene-2-carboxylic acid/2-(pyrrolidin-1-yl)ethyl, 3-tert-butyl 5-norbornene-2,3-dicarboxylate/maleic anhydride)

The procedure of Example 13 was repeated except for using 0.05 mole of 2-(pyrrolidin-1-yl)ethyl, 3-tert-butyl 5-norbornene-2,3-dicarboxylate instead of 0.05 mole of 2-(morpholin-4-yl)ethyl 5-norbornene-2-carboxylate to obtain the title compound of formula 9n in 32% yield.

EXAMPLE 27
Synthesis of poly(tert-butyl 5-norbornene-2-carboxylate/2-hydroxyethyl 5-norbornene-2-carboxylate/5-norbornene-2-carboxylic acid/2,3-di[2-(piperidin-1-yl)ethyl]5-norbornene-2,3-dicarboxylate/maleic anhydride)

The procedure of Example 13 was repeated except for using 0.05 mole of 2,3-di[2-(piperidin-1-yl)ethyl]5-norbornene-2,3-dicarboxylate instead of 0.05 mole of 2-(morpholin-4-yl)ethyl 5-norbornene-2-carboxylate to obtain the title compound of formula 9o in 31% yield.

EXAMPLE 28
Synthesis of poly(tert-butyl 5-norbornene-2-carboxylate/2-hydroxyethyl 5-norbornene-2-carboxylate/5-norbornene-2-carboxylic acid/2,3-di[2-(pyrrolidin-1-yl)ethyl]5-norbornene-2,3-dicarboxylate/maleic anhydride)

The procedure of Example 13 was repeated except for using 0.05 mole of 2,3-di[2-(pyrrolidin-1-yl)ethyl]5-norbornene-2,3-dicarboxylate instead of 0.05 mole of 2-(morpholin-4-yl)ethyl 5-norbornene-2-carboxylate to obtain the title compound of formula 9p in 34% yield.

EXAMPLE 29
Synthesis of poly(tert-butyl 5-norbornene-2-carboxylate/2-hydroxyethyl 5-norbornene-2-carboxylate/5-norbornene-2,3-dicarboxylic acid/2,3-di[2-(piperidin-1-yl)ethyl]5-norbornene-2,3-dicarboxylate/maleic anhydride)

The procedure of Example 27 was repeated except for using 0.05 mole of 5-norbornene-2,3-dicarboxylic acid instead of 0.05 mole of 5-norbornene-2-carboxylic acid to obtain the title compound of formula 9q in 32% yield.

EXAMPLE 30
Synthesis of poly(tert-butyl 5-norbornene-2-carboxylate/2-hydroxyethyl 5-norbornene-2-carboxylate/5-norbornene-2,3-dicarboxylic acid/2,3-di[2-(pyrrolidin-1-yl)ethyl]5-norbornene-2,3-dicarboxylate/maleic anhydride)

The procedure of Example 28 was repeated except for using 0.05 mole of 5-norbornene-2,3-dicarboxylic acid instead of 0.05 mole of 5-norbornene-2-carboxylic acid to obtain the title compound of formula 9r in 31% yield.

Preparation of Photoresist Compositions, and Formation of a Photoresist Pattern by Using the Same

EXAMPLE 31

The copolymer obtained from Example 13 (10 g) and triphenylsulfonium triflate (0.12 g) as a photoacid generator were dissolved in ethyl 3-ethoxypropionate (60 g), and the resultant mixture was filtered through a 0.10 μm filter to prepare a photoresist solution. The photoresist solution thus prepared was spin-coated on a silicon wafer, and soft-baked at 110° C. for 90 seconds. After baking, the photoresist was exposed to light using an ArF laser exposer, and then post-baked at 110° C. for 90 seconds. When the post-baking was completed, it was developed in 2.38 wt % aqueous TMAH (tetramethylammonium hydroxide) solution for 40 seconds, to obtain a 0.13 μm L/S pattern on the resist, having the thickness of approximately 0.45 μm.

EXAMPLE 32

The procedure of Example 31 was repeated except that the copolymer obtained from Example 14 was used instead of the copolymer of Example 13. By using this photoresist composition, 0.13 μm L/S pattern was obtained on the resist having the thickness of approximately 0.45 μm.

EXAMPLE 33

The procedure of Example 31 was repeated except that the copolymer obtained from Example 15 was used instead of the copolymer of Example 13. By using this photoresist composition, 0.13 μm L/S pattern was obtained on the resist having the thickness of approximately 0.45 μm.

EXAMPLE 34

The procedure of Example 31 was repeated except that the copolymer obtained from Example 16 was used instead of the copolymer of Example 13. By using this photoresist composition, 0.13 μm L/S pattern was obtained on the resist having the thickness of approximately 0.45 μm.

EXAMPLE 35

The procedure of Example 31 was repeated except that the copolymer obtained from Example 17 was used instead of the copolymer of Example 13. By using this photoresist composition, 0.13 μm L/S pattern was obtained on the resist having the thickness of approximately 0.45 μm.

EXAMPLE 36

The procedure of Example 31 was repeated except that the copolymer obtained from Example 18 was used instead of the copolymer of Example 13. By using this photoresist composition, 0.13 μm L/S pattern was obtained on the resist having the thickness of approximately 0.45 μm.

EXAMPLE 37

The procedure of Example 31 was repeated except that the copolymer obtained from Example 19 was used instead of the copolymer of Example 13. By using this photoresist composition, 0.13 μm L/S pattern was obtained on the resist having the thickness of approximately 0.45 μm.

EXAMPLE 38

The procedure of Example 31 was repeated except that the copolymer obtained from Example 20 was used instead of the copolymer of Example 13. By using this photoresist composition, 0.13 μm L/S pattern was obtained on the resist having the thickness of approximately 0.45 μm.

EXAMPLE 39

The procedure of Example 31 was repeated except that the copolymer obtained from Example 21 was used instead of the copolymer of Example 13. By using this photoresist composition, 0.13 μm L/S pattern was obtained on the resist having the thickness of approximately 0.5 μm.

EXAMPLE 40

The procedure of Example 31 was repeated except that the copolymer obtained from Example 22 was used instead of the copolymer of Example 13. By using this photoresist composition, 0.13 μm L/S pattern was obtained on the resist having the thickness of approximately 0.5 μm.

EXAMPLE 41

The procedure of Example 31 was repeated except that the copolymer obtained from Example 23 was used instead of the copolymer of Example 13. By using this photoresist composition, 0.13 μm L/S pattern was obtained on the resist having the thickness of approximately 0.5 μm.

EXAMPLE 42

The procedure of Example 31 was repeated except that the copolymer obtained from Example 24 was used instead of the copolymer of Example 13. By using this photoresist composition, 0.13 μm L/S pattern was obtained on the resist having the thickness of approximately 0.5 μm.

EXAMPLE 43

The procedure of Example 31 was repeated except that the copolymer obtained from Example 25 was used instead of the copolymer of Example 13. By using this photoresist composition, 0.13 μm L/S pattern was obtained on the resist having the thickness of approximately 0.5 μm.

EXAMPLE 44

The procedure of Example 31 was repeated except that the copolymer obtained from Example 26 was used instead of the copolymer of Example 13. By using this photoresist composition, 0.13 μm L/S pattern was obtained on the resist having the thickness of approximately 0.5 μm.

EXAMPLE 45

The procedure of Example 31 was repeated except that the copolymer obtained from Example 27 was used instead of the copolymer of Example 13. By using this photoresist composition, 0.13 μm L/S pattern was obtained on the resist having the thickness of approximately 0.5 μm.

EXAMPLE 46

The procedure of Example 31 was repeated except that the copolymer obtained from Example 28 was used instead of the copolymer of Example 13. By using this photoresist composition, 0.13 μm L/S pattern was obtained on the resist having the thickness of approximately 0.5 μm.

EXAMPLE 47

The procedure of Example 31 was repeated except that the copolymer obtained from Example 29 was used instead of the copolymer of Example 13. By using this photoresist composition, 0.13 μm L/S pattern was obtained on the resist having the thickness of approximately 0.5 μm.

EXAMPLE 48

The procedure of Example 31 was repeated except that the copolymer obtained from Example 30 was used instead of the copolymer of Example 13. By using this photoresist composition, 0.13 μm L/S pattern was obtained on the resist having the thickness of approximately 0.5 μm.

As shown above, the present invention provides photoresist compositions with good etching resistance, remarkably enhanced resolution of photoresist, and increased PED stability.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A bicyclic photoresist monomer selected from the group consisting of:

2-(morpholin-4-yl)ethyl 5-norbornene-2-carboxylate; 2-(morpholin-4-yl)ethyl 5-norbornene-2,3-dicarboxylate; 2-(morpholin-4-yl)ethyl, 3-tert-butyl 5-norbornene-2,3-dicarboxylate; 2,3-di[2-(morpholin-4-yl)ethyl]5-norbornene-2,3-dicarboxylate; 2-(piperidin-1-yl)ethyl 5-norbornene-2-carboxylate; 2-(pyrrolidin-1-yl)ethyl 5-norbornene-2-carboxylate; 2-(piperidin-1-yl)ethyl 5-norbornene-2,3-dicarboxylate; 2-(pyrrolidin-1-yl)ethyl 5-norbornene-2,3-dicarboxylate; 2-(piperidin-1-yl)ethyl, 3-tert-butyl 5-norbornene-2,3-dicarboxylate; 2-(pyrrolidin-1-yl) ethyl, 3-tert-butyl 5-norbornene-2,3-dicarboxylate and 2,3-di[2-(pyrrolidin-1-yl)ethyl]5-norbornene-2,3-dicarboxylate.

2. A process for preparing a bicyclic photoresist monomer of the formula:

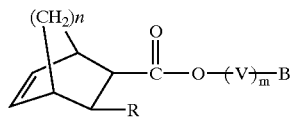

wherein

B is selected from the group consisting of moieties of the formula:

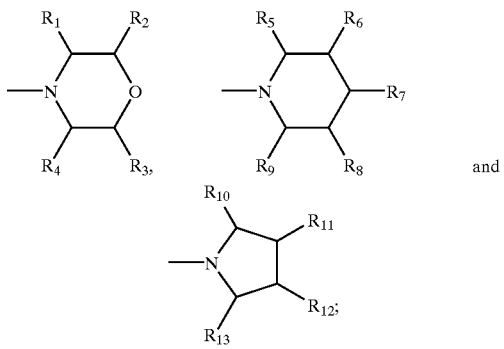

and

R is hydrogen, substituted or non-substituted ($C_1$–$C_{10}$) straight or branched chain alkyl, cycloalkyl, alkoxyalkyl, or cycloalkoxyalkyl;

V is substituted or non-substituted ($C_1$–$C_{10}$) straight or branched chain alkylene, cycloalkylene, alkoxyalkylene or cycloalkoxyalkylene;

each of $R_1$–$R_{13}$ is independently hydrogen, substituted or non-substituted ($C_1$–$C_{10}$) straight or branched chain alkyl, cycloalkyl, alkoxyalkyl, cycloalkoxyalkyl, —CH$_2$OH or —CH$_2$CH$_2$OH;

n is an integer from 1 to 3; and m is an integer from 0 to 5;

said process comprising the steps of:

(a) reacting a diene compound of the formula:

with an acrylate compound of the formula:

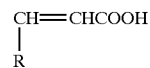

to produce a bicyclic carboxylic acid compound of the formula:

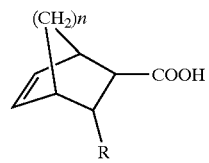

(b) reacting said bicyclic carboxylic acid compound with thionyl chloride; and (c) reacting compound produced in said step (b) with a hydroxy compound of the formula:

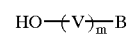

to produce said bicyclic photoresist monomer.

3. The process according to claim 2, wherein said step (a) comprises:

(i) combining said diene compound and said acrylate compound in an organic solvent at a temperature range of from about −35° C. to about −25° C.; and (ii) increasing the reaction temperature to room temperature.

4. A process for preparing a bicyclic photoresist monomer of the formula:

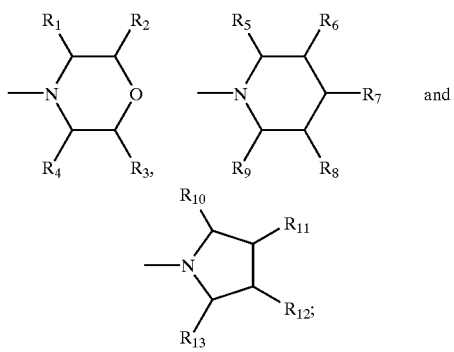

wherein

B is selected from the group consisting of moieties of the formula:

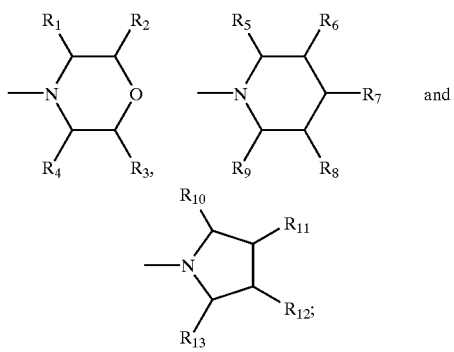

R is a moiety of the formula: —COOR' or

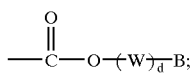

R' is hydrogen, substituted or non-substituted ($C_1$–$C_{10}$) straight or branched chain alkyl, cycloalkyl, alkoxyalkyl or cycloalkoxyalkyl;

each of V and W is independently substituted or non-substituted ($C_1$–$C_{10}$) straight or branched chain alkylene, cycloalkylene, alkoxyalkylene or cycloalkoxyalkylene;

each of $R_1$–$R_{13}$ is independently hydrogen, substituted or non-substituted ($C_1$–$C_{10}$) straight or branched chain alkyl, cycloalkyl, alkoxyalkyl, cycloalkoxyalkyl, —$CH_2OH$ or —$CH_2CH_2OH$;

n is an integer from 1 to 3; and each of d and m is independently an integer from 0 to 5, said process comprising the steps of:

(a) reacting a diene compound of the formula:

with maleic anhydride to produce 5-norbornene-2,3-dicarboxylic anhydride;

(b) (i) when R is COOR', contacting said 5-norbornene-2,3-dicarboxylic anhydride with R'OH in the presence of an acid catalyst to produce a 5-norbornene-2,3-dicarboxylate compound; or (ii) when R is

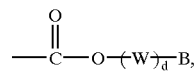

hydrating said 5-norbornene-2,3-dicarboxylic anhydride to produce a 5-norbornene-2,3-dicarboxylic acid; and (c) reacting said 5-norbornene-2,3-dicarboxylate or 5-norbornene-2,3-dicarboxylic acid compound with a hydroxy compound of the formula:

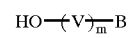

to produce said bicyclic photoresist monomer.

5. The process according to claim 4, wherein said step (a) comprises:

(i) combining said diene compound and said maleic anhydride in an organic solvent at a temperature range of from about −35° C. to about −25° C.; and (ii) increasing the reaction temperature to room temperature.

6. A photoresist copolymer derived from a monomer comprising a compound of the formula:

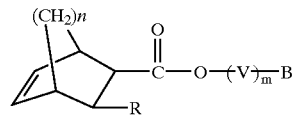

wherein

B is selected from the group consisting of moieties of the formula:

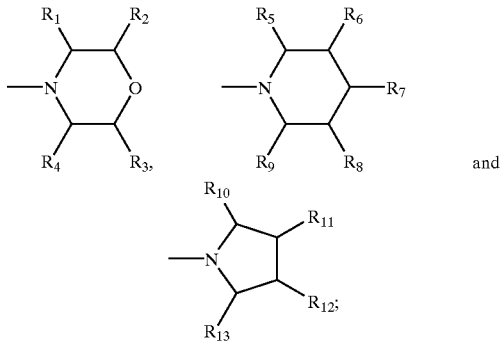

R is hydrogen, substituted or non-substituted ($C_1$–$C_{10}$) straight or branched chain alkyl, cycloalkyl, alkoxyalkyl, cycloalkoxyalkyl, —COOR', —($CH_2$)$_t$OH, —COO($CH_2$)$_t$OH or a moiety of the formula:

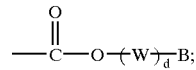

R' is hydrogen, substituted or non-substituted ($C_1$–$C_{10}$) straight or branched chain alkyl, cycloalkyl, alkoxyalkyl or cycloalkoxyalkyl;

each of V and W is independently substituted or non-substituted ($C_1$–$C_{10}$) straight or branched chain alkylene, cycloalkylene, alkoxyalkylene or cycloalkoxyalkylene;

each of $R_1$–$R_{13}$ is independently hydrogen, substituted or non-substituted ($C_1$–$C_{10}$) straight or branched chain alkyl, cycloalkyl, alkoxyalkyl, cycloalkoxyalkyl, —$CH_2OH$ or —$CH_2CH_2OH$;

n is an integer from 1 to 3; and each of d, m and t is independently an integer from 0 to 5.

7. The photoresist copolymer according to claim 6, further comprising a second monomer selected from the group consisting of a compound of the formula:

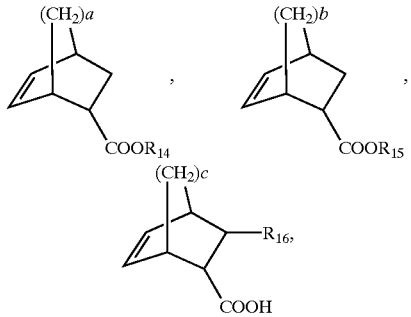

and mixtures thereof;
  wherein
  $R_{14}$ is substituted or non-substituted ($C_1$–$C_{10}$) straight or branched chain alcohol;
  $R_{15}$ is an acid labile protecting group;
  $R_{16}$ is hydrogen or —COOH; and
  a, b, and c are independently an integer from 1 to 3.

8. The photoresist copolymer according to claim 7, wherein the acid labile protecting group is selected from the group consisting of tert-butyl, tetrahydropyran-2-yl, 2-methyl tetrahydropyran-2-yl, tetrahydrofuran-2-yl, 2-methyl tetrahydrofuran-2-yl, 1-methoxypropyl, 1-methoxy-1-methylethyl, 1-ethoxypropyl, 1-ethoxy-1-methylethyl, 1-methoxyethyl, 1-ethoxyethyl, tert-butoxyethyl, 1-isobutoxyethyl and 2-acetylmenth-1-en-1-yl.

9. The photoresist copolymer according to claim 6, further comprising maleic anhydride as a third monomer.

10. The photoresist copolymer according to claim 9, which is selected from the group consisting of:

poly(tert-butyl 5-norbornene-2-carboxylate/2-hydroxyethyl 5-norbornene-2-carboxylate/5-norbornene-2-carboxylic acid/2-(morpholin-4-yl)ethyl 5-norbornene-2-carboxylate/maleic anhydride);

poly(tert-butyl 5-norbornene-2-carboxylate/2-hydroxyethyl 5-norbornene-2-carboxylate/5-norbornene-2-carboxylic acid/2-(morpholin-4-yl)ethyl 5-norbornene-2,3-dicarboxylate/maleic anhydride);

poly(tert-butyl 5-norbornene-2-carboxylate/2-hydroxyethyl 5-norbornene-2-carboxylate/5-norbornene-2-carboxylic acid/2-[2-(morphlin-4-yl) ethyl], 3-tert-butyl 5-norbornene-2,3-dicarboxylate/maleic anhydride);

poly(tert-butyl 5-norbornene-2-carboxylate/2-hydroxyethyl 5-norbornene-2-carboxylate/5-norbornene-2-carboxylic acid/2,3-di[2-(morpholin-4-yl)ethyl]5-norbornene-2,3-dicarboxylate/maleic anhydride);

poly(tert-butyl 5-norbornene-2-carboxylate/2-hydroxyethyl 5-norbornene-2-carboxylate/5-norbornene-2-carboxylic acid/(3-morpholin-4-yl-2-hydroxy)propyl 5-norbornene-2-carboxylate/maleic anhydride;

poly(tert-butyl 5-norbornene-2-carboxylate/2-hydroxyethyl 5-norbornene-2-carboxylate/5-norbornene-2-carboxylic acid/2-[(3-morpholin-4-yl-2-hydroxy)propyl]5-norbornene-2,3-dicarboxylate/maleic anhydride);

poly(tert-butyl 5-norbornene-2-carboxylate/2-hydroxyethyl 5-norbornene-2-carboxylate/5-norbornene-2-carboxylic acid/2-[(3-morpholin-4-yl-2-hydroxy)propyl], 3-tert-butyl 5-norbornene-2,3-dicarboxylate/maleic anhydride);

poly(tert-butyl 5-norbornene-2-carboxylate/2-hydroxyethyl 5-norbornene-2-carboxylate/5-norbornene-2-carboxylic acid/2,3-di[(3-morpholin-4-yl-2-hydroxy)propyl]5-norbornene-2,3-dicarboxylate/maleic anhydride);

poly(tert-butyl 5-norbornene-2-carboxylate/2-hydroxyethyl 5-norbornene-2-carboxylate/5-norbornene-2-carboxylic acid/2-(piperidin-1-yl)ethyl 5-norbornene-2-carboxylate/maleic anhydride);

poly(tert-butyl 5-norbornene-2-carboxylate/2-hydroxyethyl 5-norbornene-2-carboxylate/5-norbornene-2-carboxylic acid/2-(pyrrolidin-1-yl)ethyl 5-norbornene-2-carboxylate/maleic anhydride);

poly(tert-butyl 5-norbornene-2-carboxylate/2-hydroxyethyl 5-norbornene-2-carboxylate/5-norbornene-2-carboxylic acid/2-[2-(piperidin-1-yl)ethyl]5-norbornene-2,3-dicarboxylate/maleic anhydride);

poly(tert-butyl 5-norbornene-2-carboxylate/2-hydroxyethyl 5-norbornene-2-carboxylate/5-norbornene-2-carboxylic acid/2-[2-(pyrrolidin-1-yl)ethyl]5-norbornene-2,3-dicarboxylate/maleic anhydride);

poly(tert-butyl 5-norbornene-2-carboxylate/2-hydroxyethyl 5-norbornene-2-carboxylate/5-norbornene-2-carboxylic acid/2-[2-(piperidin-1-yl) ethyl], 3-tert-butyl 5-norbornene-2,3-dicarboxylate/maleic anhydride);

poly(tert-butyl 5-norbornene-2-carboxylate/2-hydroxyethyl 5-norbornene-2-carboxylate/5-norbornene-2-carboxylic acid/2-[2-(pyrrolidin-1-yl) ethyl], 3-tert-butyl 5-norbornene-2,3-dicarboxylate/maleic anhydride);

poly(tert-butyl 5-norbornene-2-carboxylate/2-hydroxyethyl 5-norbornene-2-carboxylate/5-norbornene-2-carboxylic acid/2,3-di[2-(piperidin-1-yl)ethyl]5-norbornene-2,3-dicarboxylate/maleic anhydride);

poly(tert-butyl 5-norbornene-2-carboxylate/2-hydroxyethyl 5-norbornene-2-carboxylate/5-norbornene-2-carboxylic acid/2,3-di[2-(pyrrolidin-1-yl)ethyl]5-norbornene-2,3-dicarboxylate/maleic anhydride);

poly(tert-butyl 5-norbornene-2-carboxylate/2-hydroxyethyl 5-norbornene-2-carboxylate/5-norbornene-2-carboxylic acid/2,3-di[2-(piperidin-1-yl)ethyl]5-norbornene-2,3-dicarboxylate/maleic anhydride); and poly(tert-butyl 5-norbornene-2-carboxylate/2-hydroxyethyl 5-norbornene-2-carboxylate/5-norbornene-2-carboxylic acid/2,3-di[2-(pyrrolidin-1-yl)ethyl]5-norbornene-2,3-dicarboxylate/maleic anhydride).

11. The photoresist copolymer according to claim 6, wherein the molecular weight of said copolymer is from about 3,000 to about 100,000.

12. A process for preparing a photoresist copolymer of claim 7 comprising the steps of:

(a) admixing
(i) a compound of the formula:

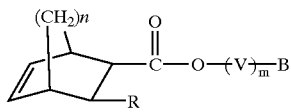

wherein

B is selected from the group consisting of moieties of the formula:

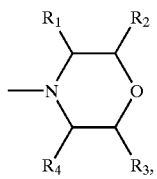 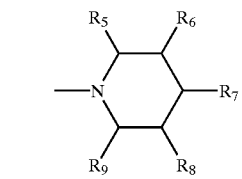 and

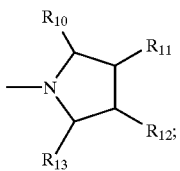

R is hydrogen, substituted or non-substituted ($C_1$–$C_{10}$) straight or branched chain alkyl, cycloalkyl, alkoxyalkyl, cycloalkoxyalkyl, –COOR', –(CH$_2$)$_t$OH, –COO(CH$_2$)$_t$OH or a moiety of the formula:

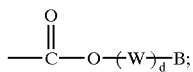

R' is hydrogen, substituted or non-substituted ($C_1$–$C_{10}$) straight or branched chain alkyl, cycloalkyl, alkoxyalkyl or cycloalkoxyalkyl;

each of V and W is independently substituted or non-substituted ($C_1$–$C_{10}$) straight or branched chain alkylene, cycloalkylene, alkoxyalkylene or cycloalkoxyalkylene;

each of $R_1$–$R_{13}$ is independently hydrogen, substituted or non-substituted ($C_1$–$C_{10}$) straight or branched chain alkyl, cycloalkyl, alkoxyalkyl, cycloalkoxyalkyl, –CH$_2$OH or –CH$_2$CH$_2$OH;

n is an interger from 1 to 3; and each of d, m and t is independently an interger from 0 to 5.

(ii) a second monomer selected from the group consisting of a compound of the formula:

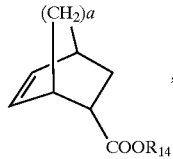 , 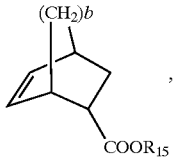 ,

-continued

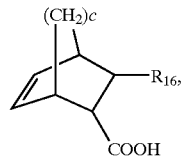

and mixtures thereof;

(iii) optionally maleic anhydride, and
(iv) a polymerization initiator; in an organic solvent; and (b) polymerizing said admixture under an inert atmosphere; wherein $R_{14}$ is substituted or non-substituted ($C_1$–$C_{10}$) straight or branched chain alcohol;

$R_{15}$ is an acid labile protecting group;

$R_{16}$ is hydrogen or —COOH;

a, b and c are independently an integer from 1 to 3.

13. The process according to claim 12, wherein said organic solvent is selected from the group consisting of cyclohexanone, tetrahydrofuran, dimethylformamide, dimethylsulfoxide, dioxane, methyl ethyl ketone, benzene, toluene and xylene.

14. The process according to claim 12, wherein said polymerization initiator is selected from the group consisting of benzoyl peroxide, 2,2'-azobisisobutyronitile (AIBN), acetyl peroxide, lauryl peroxide, tert-butyl peracetate, tert-butyl hydroperoxide and di-tert-buty peroxide.

15. A photoresist composition comprising a photoresist copolymer of claim 6, an organic solvent and a photoacid generator.

16. The photoresist composition according to claim 15, wherein said photoacid generator is a sulfide or an onium type compound.

17. The photoresist composition according to claim 15, wherein said photoacid generator is selected from the group consisting of diphenyl iodide hexafluorophosphate, diphenyl iodide hexafluoroarsenate, diphenyliodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluorophsphate, triphenylsulfonium hexafluoroarsenate, triphenylsulfonium hexafluoroantimonate, triphenylsulfonium triflate, dibutyl-naphthylsulfonium triflate, and mixtures thereof.

18. The photoresist composition according to claim 15, wherein the amount of said photoacid generator present in said composition is from about 0.05 to about 10% by weight of said photoresist copolymer.

19. The photoresist composition according to claim 15, wherein said organic solvent is selected from the group consisting of methyl 3-methoxypropionate, ethyl 3-ethoxypropionate, propylene glycol methyl ether acetate, cyclohexanone, 2-heptanone and (2-methoxy)ethyl acetate.

20. The photoresist composition according to claim 15, wherein the amount of said organic solvent present in said composition is from about 200 to about 1000% by weight of said photoresist copolymer.

21. A process for forming a photoresist pattern, said process comprising the steps of:
(a) coating a photoresist composition of claim 15 on a substrate of semiconductor element to form a photoresist film;
(b) exposing said photoresist film to light using a light source; and
(c) developing said photoresist film.

22. The process for forming a photoresist pattern according to claim 21 further comprising heating said photoresist film before said step (b), after said step (b), or combinations thereof.

23. The process for forming a photoresist pattern according to claim 22, wherein said photoresist film is heated to a temperature range of from about 70° C. to about 200° C.

24. The process for forming a photoresist pattern according to claim 21, wherein said light source is ArF, KrF, EUV, VUV, E-beam, X-ray or Ion-beam.

25. The process for forming a photoresist pattern according to claim 21, wherein said photoresist film is irradiated with light-exposure energy in the range of from about 1 mJ/cm$^2$ to about 100 mJ/cm$^2$.

26. A semiconductor element manufactured by the process according to claim 21.

* * * * *